United States Patent
Mulye

(10) Patent No.: US 6,946,146 B2
(45) Date of Patent: Sep. 20, 2005

(54) COATING FOR A SUSTAINED RELEASE PHARMACEUTICAL COMPOSITION

(75) Inventor: Nirmal Mulye, Princeton, NJ (US)

(73) Assignee: Nostrum Pharmaceuticals Inc., Princeton, NJ (US)

( * ) Notice: Subject to any disclaimer, the term of this patent is extended or adjusted under 35 U.S.C. 154(b) by 0 days.

(21) Appl. No.: 10/124,869

(22) Filed: Apr. 18, 2002

(65) Prior Publication Data

US 2002/0155156 A1 Oct. 24, 2002

Related U.S. Application Data

(60) Provisional application No. 60/284,463, filed on Apr. 18, 2001.

(51) Int. Cl.$^7$ .............................. A61K 9/30; A61K 9/32; A61K 9/36; A61K 9/38
(52) U.S. Cl. ...................... 424/479; 424/474; 424/475; 424/477; 424/480; 424/482; 424/491; 424/493; 424/494; 424/495; 424/497
(58) Field of Search ................................ 424/465, 490, 424/494, 495, 497, 474, 475, 479, 480, 482, 493, 477, 491

(56) References Cited

U.S. PATENT DOCUMENTS

| 4,330,338 A | * | 5/1982 | Banker | 106/162.82 |
| 4,963,365 A | | 10/1990 | Samejima et al. | 424/493 |
| 5,126,146 A | * | 6/1992 | Seminoff et al. | 424/468 |
| 5,595,762 A | | 1/1997 | Derrieu et al. | 424/490 |
| 6,251,432 B1 | * | 6/2001 | Mazer et al. | 424/480 |

* cited by examiner

*Primary Examiner*—James M. Spear
(74) *Attorney, Agent, or Firm*—Scully, Scott, Murphy & Presser

(57) ABSTRACT

The present invention is directed to a coating composition for coating a solid dosage form of a medicament, where the coating composition controls the release of the medicament, said coating composition comprising (a) at least 50% (w/w) by dry weight of a water insoluble polymer insoluble in both acidic, basic and neutral pH, present in the form of an aqueous latex dispersion, (b) a water soluble non-polymeric component present in a weight ratio of about 5 to about 50% (w/w) by dry weight of the coating, having a molecular weight of less than about 15,000 daltons and water solubility in excess of 5 grams per 100 grams of water at room temperature at 1 atm pressure, said water soluble non-polymeric component being organic and either solid or liquid; said ratio of water insoluble polymer to water soluble non-polymeric component ranging from about 95:5 to about 1:1, the solid content in the coating composition ranges from about 5% to about 25%, said water soluble component being completely dissolved in the aqueous latex dispersion. The present invention is also directed to a system for the controlled release of an active medicament comprising a substrate and a coating, said substrate comprising a therapeutically effective amount of a medicament in association with a pharmaceutical carrier in solid unit dosage form, said substrate being uniformly coated with the aforesaid coating composition.

75 Claims, 3 Drawing Sheets

COATING FOR A SUSTAINED RELEASE PHARMACEUTICAL COMPOSITION

CROSS-REFERENCE TO RELATED APPLICATION

The present application claims priority of provisional application Ser. No. 60/284,463, filed on Apr. 18, 2001.

FIELD OF THE INVENTION

This invention relates to a controlled release formulation of a therapeutic agent and in particular, to a sustained release formulation in which a solid substrate containing the active ingredient is provided with a coating which regulates the release of the active ingredient.

BACKGROUND OF THE INVENTION

Solid pharmaceutical or other functionally active preparations which ensure a sustained release of active ingredients over a long period of time are well known in the art. These sustained release compositions are designed to contain higher concentrations of the active ingredient than conventional, immediate release dosage forms, and they are prepared in such a manner as to effect sustained or slow release of the active ingredient into the gastrointestinal digestive tract of humans or animals over an extended period of time. Well absorbed solid oral sustained release therapeutic drug dosage forms have inherent advantages over the conventional, immediate release drugs. These delayed release forms make it possible to reduce the number of doses of the drug to be administered daily, thereby facilitating patient compliance with the treatment plan prescribed by the physician. Moreover, they ensure a constant concentration of active ingredient in the body and a more sustained drug blood level response. Moreover, by utilizing a sustained release formulation, therapeutic action is effected though less drug relative to conventional immediate release dosage forms is absorbed in the gastrointestinal tract at a given time, thereby mitigating side effects associated with a particular drug. By providing a slow and steady release of the drug over time, absorbed drug concentration spikes are mitigated or eliminated by effecting a smoother and more sustained blood level response.

Many sustained release formulations, especially those in tablet and capsule form are provided with a coating which regulates the release of active ingredient. Various coating techniques have been utilized heretofore to control the rate or the site of the release of the active ingredient in the pharmaceutical formulation.

U.S. Pat. No. 4,016,880 to Theewees, et al. describes a sustained release coating on a tablet having an osmotic solute therein. The coating has a controlled permeability to water. The drug is released through passages in the coating formed at the sites of structural weaknesses therein. The technology requires the polymers to be dissolved in organic solvents and the coating is effected by using organic solvents.

Wong, et al. in U.S. Pat. No. 4,765,989 describe an osmotic system comprising a wall comprising, in at least a part, of a semipermeable material that surrounds a compartment. The compartment contains an osmotic composition comprising a drug, e.g., nifedipine, prazosin, and doxazosin, and a second and different osmotic composition. A passageway in the wall connects the first osmotic composition with the exterior of the system. The technology requires the polymers to be dissolved in organic solvents and the coating is effected by using organic solvents.

U.S. Pat. No. 5,840,335 to Wenzel, et al. describes a system for the controlled release of an active agent wherein the system has a predetermined release rate of the active ingredient to the environment of use, and comprises (a) a shell comprised of a wall formed of a water-insoluble material which is permeable to the passage of an external fluid and (b) a core which is surrounded by said shell, the core being comprised of a water soluble active agent and a soluble polymeric adjuvant, such as polyvinyl alcohols, preferably with a residual context of 6 to 18% and an average molecular weight of 20,000 to 70,000 and a cellulose compound such as methyl cellulose, methylethylcellulose, hydroxypropylcellulose, hydroxypropylmethyl cellulose and carboxymethyl cellulose, capable of unlimited swelling. The technology requires the polymers to be dissolved in organic solvents and the coating is effected by using organic solvents.

U.S. Pat. Nos. 4,880,631 and 4,886,668 to Haslam, et al. are directed to osmotic pumps, for the controlled release of an active substance, diltiazem, L-malate to an environment of use, said pump comprising (a) a core which comprises a therapeutically effective amount of diltiazem L-malate and an effective buffering amount of sodium bitartrate surrounded by a rate controlling water insoluble wall. The coating utilizes a polymer permeable to water but impermeable to solute and a pH insensitive pore forming additive dispersed through the wall. The drug is released through the pore followed by the movement of water under an osmotic gradient across the wall. The technology requires the polymers to be dissolved in organic solvents and the coating is effected by using organic solvents.

Chen, et al. in U.S. Pat. No. 5,736,159 discloses a controlled release pharmaceutical tablet based on
 (a) a compressed core which contains:
  (i) a medicament;
  (ii) at least 23% to 55% by weight, based on the total weight of the core, of a water soluble osmotic agent;
  (iii) a water soluble pharmaceutically acceptable polymer binder;
  (iv) a water-swellable pharmaceutically acceptable polymer;
  (v) a conventional pharmaceutical excipient, and
 (b) a membrane coating around the core tablet consisting essentially of:
  (i) a modified water insoluble pharmaceutically acceptable polymer; and
  (ii) a pharmaceutically acceptable water soluble polymer.

U.S. Pat. No. 5,458,887 to Chen, et al. discloses a controlled release dosage form which comprises:
 (a) an osmotic core consisting essentially of a drug and water swellable component selected from the group consisting of hydroxypropylmethyl cellulose and polyethylene oxide in admixture with the drug; and
 (b) a coating comprising a water resistant polymer and a minor amount of a non-toxic water soluble pharmaceutically acceptable compound in an amount which is sufficient to dissolve in the gastrointestinal fluid and form a plurality of micropores on the outside of the tablet, the water resistant polymer being microporus to the passage of the gastrointestinal fluid. A pathway for drug release is created when the water soluble material, e.g., salt crystals, is dissolved when it comes in contact with the aqueous medium. The technology requires the polymers to be dissolved in organic solvents and the coating is effected by using organic solvents.

Baker, et al. in RE 33,994 are directed to a pharmaceutical composition for use in an aqueous environment which comprises a formulation containing a water-soluble pharmaceutically medicament, a water-insoluble, water-permeable film coating surrounding the formulation and a particulate water soluble pore-forming material dispersed within the film coating. The coating is prepared by dissolving the water insoluble film in an organic solvent and adding thereto the pore-forming material and a water modifying agent, if necessary.

U.S. Pat. No. 5,376,388 to Eichel, et al. describes a coating where the permeability is controlled by the rate of hydration of the coating. The hydratable diffusion barrier surrounds a water-soluble drug-core and comprises a film-forming polymer such as an acrylic resin or ethyl cellulose and an additive which controls the rate of hydration and permeability of the hydratable diffusion barrier selected from the group consisting of fully esterified acrylic resins containing quaternary amin side chains, lubricant anionic surfactants, plasticizers, inert water soluble materials and mixtures thereof. The rate of hydration is controlled by the selection of the polymer and various additives.

U.S. Pat. No. 4,060,598 to Groppenbächer, et al. discloses coated pharmaceutical tablets prepared by applying to a core of active material, at least one layer of a coating composition made up of a film forming aqueous synthetic resin dispersion and from 2–50% by weight of a water or alkaline soluble material and thereafter permitting the coating composition to dry. The resulting coated tablet has a core surrounded by a continuous porous matrix of synthetic resin formed from the aqueous dispersion which is insoluble in water and insoluble in the gastrointestinal tract. The pores of the continuous resin matrix are filled with a discontinuous particulate material which is water or alkaline soluble. In other words, the coating is not a continuous phase. The coated tablet initially is air and moisture tight. They describe the coating as achieving fast disintegrating or enteric disintegrating coating for tablets.

U.S. Pat. No. 5,759,577 to Barcomb discloses a compressed medicinal tablet comprising a tablet core and a sugar coating, where the sugar contains a dose of a hormonal steroid, a drug and a steroid release rate controlling amount of microcrystalline cellulose, and PVP to aid in application of the sugar coat. In Barcomb, the major portion of the coating contains the sugar, and a minor portion contains the drug, i.e., steroidal hormone, and if present, the PVP.

U.S. Pat. No. 4,248,856 to Guley, et al. describes the use of sugar coating in conjunction with a barrier coating on a core containing medicament in order to provide controlled release of pharmaceuticals. More particularly, U.S. Pat. No. 4,248,856 describes a sustained release pharmaceutical composition comprising a compressed core containing a drug, a seal coating surrounding the core and a sugar coating surrounding the seal coated core wherein, (a) the core comprises a therapeutically effective amount of at least one drug in an amount of about 29% to about 64% by weight of the core, and the cellulose polymers hydroxypropyl methylcellulose and ethylcellulose in an amount of 30% to about 45% by weight of the core;

(b) the seal coating comprises an enteric coating material; and (c) the sugar coating comprises sugar and a loading dose of at least one drug contained in the core in which the ratio of the drug in the sugar coating and the drug in the core is from about 1:15 to about 1:4.3.

In short, many of the technologies described in the prior art hereinabove have a common feature, a rate controlling membrane surrounding a core. In many of the aforementioned references, the membrane is made from water insoluble polymers, and various additives are added in various forms to alter the permeability of the membrane to allow and control the rate of release of drug. Most of them require the use of organic solvents. Some of them require the presence of certain ingredients, e.g., osmotic ingredients, for the formulation to function.

However, unlike the systems described hereinabove, the present invention is directed to a new and novel coating composition. In the novel coating composition of the present invention, the insoluble polymer is present in an aqueous dispersion form and the permeability as well as the strength of the membrane is adjusted by using an appropriate amount of an inert, low molecular weight water soluble ingredient which is homogeneously dispersed throughout the aqueous dispersion. As described hereinbelow, the coating composition of the present invention has several advantages over coating compositions described in the prior art or commercially used.

SUMMARY OF THE INVENTION

Accordingly, the present invention is directed to a system for the controlled release of an active agent comprising a core and a coating of said core, said core comprising the active agent and a pharmaceutically acceptable carrier, and the coating comprising a homogeneous mixture of:

(a) an insoluble polymer which is insoluble in acidic, neutral and basic pH aqueous solution, but which is present in an aqueous latex dispersion, said polymer being present in at least 50% of the dry weight of the coating;

(b) a low molecular weight water soluble non polymeric compound present in amounts ranging from about 5% to about 50% by dry weight of the coating, said non-polymeric compound having a molecular weight of less than about 15,000 daltons and being substantially soluble in water at 25° C. and 1 atm pressure, said water soluble component being dissolved in the latex dispersion and homogeneously dispersed therethrough.

The present invention is also directed to a coating composition for coating an oral dosage form of a pharmaceutical composition and controlling the release of the active ingredient therefrom, said coating comprising the homogeneous mixture defined hereinabove.

In another embodiment, the present invention is directed to a method of treating a patient with an orally administrable time-release drug comprising: administering to said patient the time-release orally administrable drug comprising the drug composition described hereinabove. The invention is also directed to a method of preparing a sustained release pharmaceutical which comprises coating the medicament with the coating described hereinabove.

DETAILED DESCRIPTION OF THE PRESENT INVENTION

Figure 1:
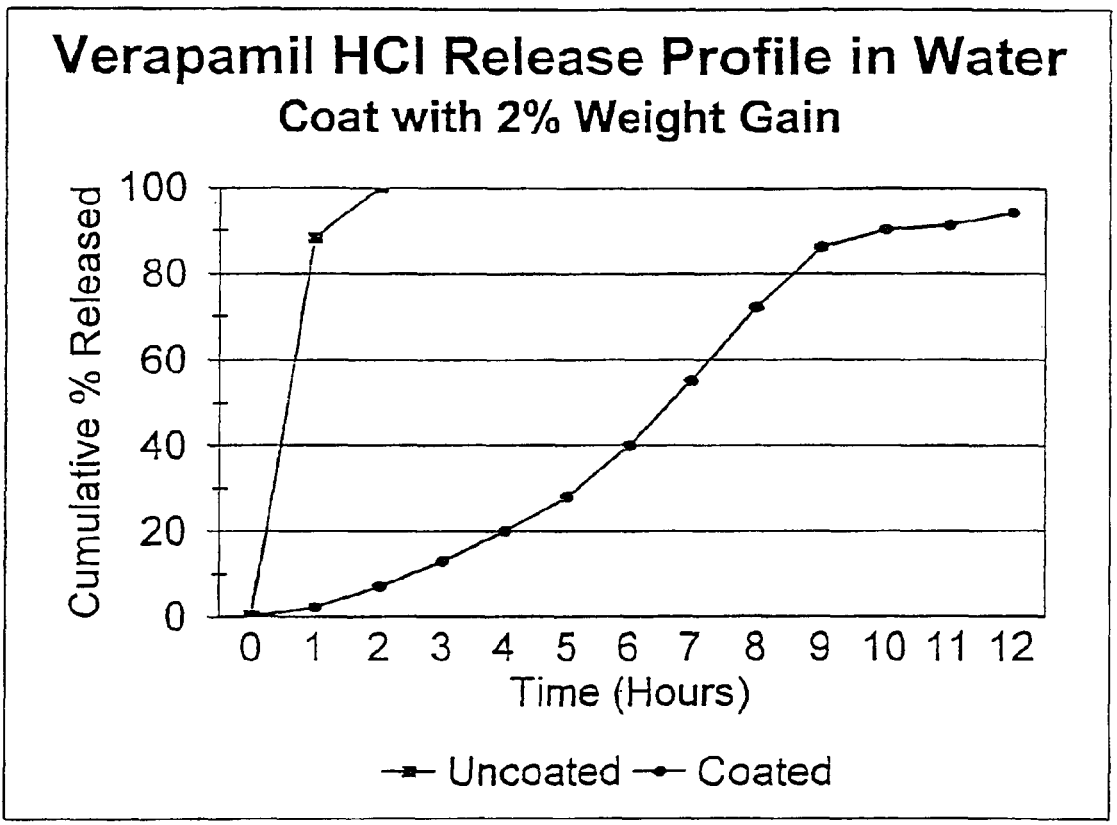
FIG. 1 graphically compares the dissolution rate of a Verapamil tablet in water without a coating and with a coating prepared in accordance with the present invention.

The coating composition of the present invention may be used to coat various cores or substrates containing the active ingredient such as tablets, spheroids (or beads), microspheres, seeds, pellets, or other multi-particulate systems, in order to obtain a desired controlled release of the active agent. Granules, spheroids, pellets, and the like can be presented in a capsule or in another suitable dosage form. The tablets can be any suitable shape, such as round, oval, biconcave, hemispherical or any polygonal shape, such as square, rectangular, pentagonal and the like. The cores contain the medicament or therapeutically active agent which is administered to the patient, e.g., animal and more preferably mammal.

By mammal, it is meant vertebrae of the class of mammalia that is characterized by possession of hair and mammary glands. Examples include, inter alia, dog, cat, horse, pig, goat, cow, human being and the like. The preferred species of mammal to which the sustained release formulation of the present invention is to be administered is man.

The term "sustained release" and "controlled release" are being used interchangeably. As used herein, they refer to the release of the active ingredient at such a rate that blood levels are maintained within the therapeutic range but below toxic levels over an extended period of time, e.g., 4 to 24 hours or even longer.

The term "bioavailability" as used herein refers to the extent to which the active drug ingredient is absorbed from the pharmaceutical formulation and is available at the site of drug action.

The coating formulations of the present invention are capable of producing a strong continuous film that is smooth and elegant that completely and uniformly or substantially uniformly surrounds the core. The coating composition of the present invention is non-toxic, capable of supporting pigments and other coating inert additives.

The first component of the coating is the water insoluble polymer. It is insoluble in water at 25° C. and 1 atm pressure. More specifically, it is insoluble or substantially insoluble in aqueous solution at acidic, neutral and basic pH's at 1 atm pressure and at room temperature. By "substantially insoluble in aqueous solution in acidic, neutral or basic pH's", it is meant that the polymer is substantially insoluble in aqueous solution, regardless of the pH. Its solubility in aqueous solution is therefore independent of the pH. The polymeric compound is not soluble in the gastrointestinal fluids. The term "pH independent" as used herein means that the water permeability thereof and hence its ability to release pharmaceutical ingredients is not a function of pH and/or is only very slightly dependent on pH. Accordingly, the sustained release formulations of the present invention are capable of releasing active ingredient at a controlled rate which is independent of physiological factors, such as pH, which can vary from one subject to another and can vary from time to time for a particular subject.

The insoluble polymer is a pharmaceutically acceptable non-toxic polymer substantially insoluble in aqueous media, e.g. water, independent of the pH thereof. Thus, it is insoluble in the gastric fluid, i.e., at pH's of less than 4 and is insoluble in the intestinal fluid, i.e., at pH's between 6.0 and 7.5 and at the various pH's between 6.0 and 7.5 and at the various pH's between 4 and 6 at 25° C. It also is insoluble in water at pH's greater than 7.5 at 25° C. The polymer may be a cellulose ether, cellulose ester, or cellulose ether-ester, i.e., a cellulose derivative in which (a) part of the hydroxy groups on the cellulose skeleton are substituted with alkyl groups, preferably containing 1–10 carbon atoms and more preferably lower alkyl groups (i.e., alkyl groups containing 1–6 carbon atoms) or (b) the hydroxy groups are substituted with lower alkanoyl, that is,

wherein alkyl is as defined herein.

In view of the requirement that the insoluble polymer is substantially insoluble in both gastric and intestinal fluids, those cellulose derivatives having a minimal number of hydrophilic substituents are preferred. Examples include ethyl cellulose, acetyl cellulose, nitrocellulose, and the like.

Other examples of insoluble polymers include lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, which is a water insoluble film former based on a neutral swellable methacrylic acids esters with a small proportion of trimethylammonioethyl methacrylate chlorides, the molar ratio of the quaternary ammonium groups to the neutral ester group is 1:40 (~25 meg/100 g); EUDRAGIT RL®, which is also a water insoluble swellable film former based on neutral methacrylic acid esters with a small portion of trimethylammonioethyl methacrylate chloride, the molar ratio of quaternary ammonium groups to the neutral ester group is 1:20 (corresponding to about 50 meg/100 g); EUDRAGIT NE®, which is a neutral methacrylic acid ester without any functional groups that form a water insoluble film and the like. Preferred insoluble polymers useful in the present invention include polyvinyl esters, polyvinyl acetals, polyacrylic acid esters, butadiene styrene copolymers, and the like.

The more preferred water insoluble polymers used in the present invention are ethyl cellulose, polyvinyl acetate, cellulose acetate, and ethyl cellulose is the most preferred insoluble polymer.

The insoluble polymer is in the form of an aqueous latex dispersion. By "latex dispersion" is meant a synthetic resin dispersion in water. It is a durable milky dispersion of solid particles of the water insoluble polymer having an average particle size of 0.2–3 microns. It is similar to natural rubber latex. As an aqueous synthetic resin dispersion for the coating composition according to the present invention, any of the pharmacologically compatible, insoluble polymeric film formers described hereinabove can be used. Thus, for example, there can be used aqueous dispersions of any of the aforementioned insoluble polymers, including latex dispersions of polyvinyl esters, polyvinyl acetals, polyacrylic acid esters, cellulose ethers, cellulose esters, butadiene styrene copolymers, methacrylic and acrylate polymers, and the like. It is more preferred that water insoluble polymers selected from the group consisting of ethyl cellulose, polyvinylacetate, and cellulose acetate, but in the form of a latex dispersion. It is most preferred that ethyl cellulose is in a latex dispersion.

Suitable latex dispersions of ethyl cellulose include those available under the tradenames AQUACOAT ECD-30® from FMC Corporation (Philadelphia, USA) and SURELEASE® from Colorcon (West Point, Pa.). AQUACOAT® is an aqueous polymeric dispersion of ethylcellulose and contains sodium lauryl sulfate and cetyl alcohol while SURELEASE® is an aqueous polymeric dispersion of ethyl cellulose and contains dibutyl sebacate, oleic acid, ammoniated water and fumed silica.

As indicated hereinabove, the insoluble polymer comprises at least 50% by dry weight of the coating. More preferably, it is present from 50% to 95% by dry weight of the coating. More preferably, the insoluble polymer is present in at least about 60% by dry weight of the coating. It is thus preferred that the insoluble polymer is present in an amount ranging from about 60% by dry weight up to and including about 90% by dry weight of the coating and more preferably from and including about 70% dry weight up to and including about 80% by dry weight of the coating.

The aqueous dispersions can be produced by art recognized techniques, such as by known emulsion polymerization techniques.

The second component in the coating is the water soluble compound which has a molecular weight of 15,000 daltons or less and more preferably less than about 10,000 daltons, and most preferably less than about 2000 daltons and even more preferably less than 1000 daltons. The molecular weight of the water soluble compound is at least about 40 and more preferably is at least about 50. The preferred molecular weights of the soluble compound ranges from about 50 to about 1000 daltons.

The water soluble compound is soluble in water but is not soluble in the polymer. It has a solubility in water of greater than 1 gram per 100 grams of water at room temperature and 1 atm pressure. It is an organic compound. It is preferably a solid, but it may also be a liquid. Examples include sugars, amino acids, bulking agents, such as polydextrose, organic acids, or salts thereof glycerin, glycols, and the like. Preferred examples include monosaccharides, disaccharides, such as lactose or sucrose, glycerine, propylene glycol, or salts thereof, sugar alcohols, polydextrose and the like.

As used herein, the monosaccharides contain from 3–6 carbon atoms and include aldoses and hexoses. Examples of monosaccharides include glyceraldehydes, erythrose, threose, ribose, arabinose, xylose, lyxose, allose, altrose, glucose, mannose, idose, galactose, talose, erythrulose, ribulose, xylulose, psicose, fructose, sorbose, tagatose, and the like. The monosaccharides may exist as either the D or L isomer, although the D-isomer is preferred.

Examples of disaccharides utilized in the polymerization include maltose, lactose, sucrose and the like.

The most preferred low molecular weight water soluble agents are sugars, especially lactose and most especially sucrose.

It is preferred that the low molecular weight water soluble component is non-ionic in nature because high concentrations of ionic material may cause coalescence of the latex dispersion, which may render it un-usable.

The low molecular weight water soluble agent is present in at least 5% (w/w) of the dry weight of the coating and not more than about 50% of the dry weight of the coating (w/w). More preferably, it is present from about 10% to about 40% of the coating (dry weight) and more preferably from about 20% to about 30% of the coating (dry weight). In addition, the dry weight ratio of the insoluble polymer to the water soluble low molecular weight non-polymeric component is greater than or equal to 1:1, and more preferably ranges from about 11:9 to about 9:1 and even more preferably from about 13:7 to about 17:3 and most preferably from about 7:3 to about 8:2.

The soluble component is completely soluble in the aqueous dispersion containing the insoluble polymer.

It is critical that the soluble component is substantially and more preferably completely soluble in the coating dispersion. Upon formation of the coat, the soluble component is uniformly dispersed in the coating composition. It is critical that the latex dispersion and therefore the coating composition is water based in order to completely dissolve the water soluble ingredient. Thus, the pores in the matrix of the coating composition of the present invention do not contain discontinuous particulate materials. The coating composition of the present invention is in a continuous phase.

The coating composition contains at least about 5% solids with the remainder being water prior to its application to the solid dosage unit form. More preferably, the coating composition contains from about 5% to about 25% solids, and more preferably from about 10% to about 15% (w/w).

Besides the water insoluble polymer in a latex dispersion, the water soluble compound, and the water, the coating composition may also contain other additives normally found in coatings used in the pharmaceutical art. These include plasticizers, wetting agents commonly used in pharmaceutical compositions, lubricants, coloring agents, taste masking agents, commonly used in the pharmaceutical compositions and the like.

The coloring agents are added to provide elegance and product distinction. Suitable ingredients for providing color to the formulation include titanium dioxide and color pigments, such as iron oxide pigments, FD&C Yellow No. 6, FD&C Red No. 2, FD&C Blue No. 2, food lakes and the like. If present, they are present in amounts ranging from about 0.1% to about 20% by dry weight of the coating (w/w) and more preferably less than about 3% by dry weight (w/w).

The plasticizer may be selected from those plasticizers normally used in coating compositions of pharmaceuticals. Examples include diethylphthalate, triethyl citrate, triethyl acetyl citrate, triacetin, tributylcitrate, polyethylene glycol, glycerol, vegetable and mineral oils, maltodextrin and mixtures thereof, and the like. It will be understood that the plasticizer used may be largely dictated by the polymer used in the coating composition. The plasticizer may be present in the coating in amounts ranging from about 0.01% to about 25% by weight and more preferably from about 5 to about 15% by weight based on the dry weight of the coating.

The coating layer may optionally include a lubricant. Examples of suitable lubricants include talc, calcium stearate, colloidal silicon dioxide, glycerin, magnesium stearate, aluminum stearate, or a mixture of any two or more of the forgoing, and the like. If present, the lubricant is present in amounts ranging from about 0.01% to about 10% by dry weight of the coating.

The coating is prepared by art recognized techniques. The insoluble polymer in the latex dispersion is either commercially prepared or is prepared using known emulsion polymerization techniques. It is mixed with the water soluble organic compound, and additional water, if further dilution is desired until the water soluble inorganic compound is completely dissolved in the coating dispersion, i.e., uniformly dispersed in the coating dispersion. The coating dispersion is prepared by dissolving the water soluble ingredient in water and adding the latex dispersion of the insoluble polymer to it and then mixing the two together until the water soluble ingredient is dissolved in the aqueous dispersion. Alternatively, the coating dispersion is prepared by adding water to the latex dispersion of the insoluble polymer and then dissolving the water soluble component in the diluted dispersion. Whichever way made, the coating dispersion has a solid content ranging from about 5% to about 25% w/w, preferably from about 10% to about 20%, more preferably from about 10% to about 15% w/w of the aqueous dispersion. Whichever way made, the remaining optional ingredients are then added and mixed until completely dissolved or until additional optional components become dissolved.

The coating is applied to the core as described hereinbelow.

A wide variety of therapeutically active agents can be used in conjunction with the present invention. Examples include antacids, anti-inflammatory substances, coronary dilators, cerebal dilators, peripheral vasodilators, anti-invectives, psychotropics, anti-maniics, stimulants, anti-histamines, laxatives, decongestants, vitamins, gastro-intestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypogly-cemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics anti-uricemic drugs and the like. Typical active ingredients include gastro-intestinal sedatives such as metoclopramide and propantheline bromide; antacids such as aluminum trisilcate, aluminium hydroxide and cimetidine; anti-inflammatory drugs such as phenylbutazone, indomethacin, naproxen, ibuprofen, fluriprofen, diclofenac, dexamethasone, prednisone and prednisolone; coronary vasodilator drugs such as glyceryl trinitrate, isosorbide dinitrate and pentaerythritol tetranitrate; peripheral and cerebal vasodilators, such as solocidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, dioxepin, lithium carbonate, lithium sulfate, chlorpromazine, thioridazine, trifluoroperazine, fluphenazine, piperothiazine, haloperidol, maprotiline hydrochloride, imipramine and desmethylimipramine; central nervous stimulants such as methylphenidate ephedrine, epinephrine, isoproterenol, amphetamine sulfate and amphetamine hydrochloride; anti-histamic drugs such as diphenhydramine, diphenylpyraline, chlorphenitamine and brompheniramine; laxative drugs such as bisacodyl and magnesium hydroxide; dioctyl sodium sulfosuccinate; nutritional supplements such as ascorbic acid, alpha tocopherol, thiamine and pyridoxine; anti-spasmadic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protaminc sulfate; analgesic drugs such as acetylsalicylic acid, acetaminophen, tramadol, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, and mefenamic acid; anti-epileptic drugs such as phenytoin sodium and sodium valproate; neuromuscular drugs such as dantrolene sodium; substances used in the treatment of diabetes such as tolbutamide, glipiside, disbenase glucagon and insulin; drugs used in the treatment of thyroid gland disfunction such as triiodothyronine, thyroxine and propylthiouracil; diuretic drugs such as furosemide, chlorthalidone, hydrochlorothiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; hemopoietic drugs such as ferrous sulphate, folic acid and calcium gluconate; uricosuric drugs such as sulphinpyrazone, allopurinol and probenecid.

The medicaments are present in pharmaceutically effective amounts. It is preferred that the medicament is present in amounts ranging from about 0.5% to about 90% by dry weight of the unit dosage form.

The active ingredient is associated with a pharmaceutical carrier in the core. These include lubricants, excipients, such as plasticizers and fillers, and the like.

Fillers, such as maltodextrin, sugar, lactose, and microcrystalline cellulose may also be present. They are preferably present in amounts ranging from about 2% to about 70% by weight of the carrier, and more preferably from about 10% to about 50% of the carrier and most preferably from about 20% to about 40% by weight of the carrier.

One of ordinary skill in the art understands that excipients, e.g., fillers or plasticizers, have several functions in the pharmaceutical composition. For example, they may be added to enhance tableting characteristics or increase the bulk of the pharmaceutical composition. It is within the purview of one of ordinary skill in the art to determine how much excipient is to be added and the objective that he wishes to accomplish by adding the same. The amounts given hereinabove for the fillers are to be understood as preferred embodiment.

Other optional ingredients that are also typically used in pharmaceuticals may also be present, either in the core or in the coating composition such as coloring agents, preservatives (e.g., methyl parabens), artificial sweeteners, flavorants, anti-oxidants, and the like.

If the unit dosage form is in the form of a pellet, then the pellet is prepared by techniques known in the art. In a pellet, the active ingredient in a solution or suspension is layered on starter particles, e.g., a substrate which is preferably a sphere, bead or seed. The starter particles or seeds can be any free flowing nonfriable granular material such as sucrose or lactose or can be crystals of the active ingredient which serve as starter seeds. Preferably, it is a sugar or starch sphere having an average diameter of from about 0.5 mm to about 1.5 mm.

In addition to the active ingredient or drug, the pellet also preferably contains a binder. A binder promotes adhesion of the drug to the beads and is present in binding effective amounts. Preferably, the binding agent is present in amounts of from about 0.1 to about 45% by weight of the core element and more preferably from about 0.1 to about 20% by weight and most preferably approximately about 3 to about 15% by weight, based on the total weight of the core element.

The binding agent may be any suitable type used in the pharmaceutical arts. Suitable binders may be selected from polyvinyl-pyrrolidine, hydroxypropyl cellulose, hydroxypropyl methyl cellulose, sugars (e.g., glucose), acacia, carboxymethylcellulose sodium, dextrin, ethylcellulose, gelatin, pregelatinized starch, sodium aldinate, zein, and the like or mixtures thereof. The binding agent may be provided in the form of a granulating solution. An aqueous or organic solvent may be included. Methanol, ethanol or mixtures thereof may be used as solvents.

Besides the active ingredient and a binder that promotes adhesion of the drug to the starter seeds, the core may also contain antiadherents that prevent or minimize agglomeration during the layering process, and other ingredients such as those described hereinabove.

The active ingredient in the core may be associated with a swelling agent known in the art.

The swellable polymer materials may additionally be hydrogels that swell in, and retain a significant amount of water. Polymeric hydrogels (which can be crosslinked and uncrosslinked) swell or expand significantly in water, usually exhibiting a 2 to 50 fold or greater volume increase. The crosslinked polymers will swell and will not dissolve; uncrosslinked polymers may dissolve subsequent to swelling although dissolution is not a necessary consequence. Examples of swellable polymers useful in the formulation of the present invention include: crosslinked polymethacrylate and polyacrylate polymers derivatized with hydroxyalkyl and/or ionizable acidic or basic functional groups, and their respective salt forms, crosslinked polyvinyl pyrrolidone; crosslinked polyvinyl alcohols; poly(ethylene oxide)s; polymethacrylamides and polyacrylamides; crosslinked hydroxypropylcellulose, starch graft copolymers, crosslinked hydroxypropylmethylcellulose, crosslinked dextrans and agarose, and microcrystalline cellulose; carboxymethylamide; and polyelectrolytes.

Suitable pharmaceutically acceptable, water swellable polymers include polyethylene oxide having a molecular weight of 100,000 to 5,000,000; poly(hydroxy alkyl methacrylate) having a molecular weight of from 30,000 to 5,000,000; poly(vinyl) alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a water insoluble, water swellable copolymer produced by forming a dispersion of a finely divided copolymer of maleic anhydride with styrene, ethylene, propylene, butylene or isobutylene cross-linked with from 0.001 to 0.5 moles of saturated cross-linking agent of saturated cross-linking agent per mole of maleic anhydride in the copolymer; Carbopol® acidic carboxy polymers having a molecular weight of 450,000 to 4,000,000; Cyanamer® polyacrylamides; cross-linked water swellable indene-maleic anhydride polymers; Goodrite® polyacrylic acid having a molecular weight of 80,000 to 200,000; starch graft copolymers; Aqua-Keeps® acrylate polymer polysaccharides composed of condensed glucose units such as diester cross-linked polyglucan and the like. Other polymers which form hydrogels are described in U.S. Pat. Nos. 3,865,108; 4,207,893 all of which are incorporated by reference. The pharmaceutically acceptable, water swellable polymers may be employed in an effective amount that will control the swelling of the tablet core. These amounts will generally be from about 3 to about 25 wt %, preferably from about 5 to about 20 wt % based on the weight of the core.

The coating composition of the present invention is coated onto the core containing a drug in any conventional oral unit dosage form, such as a tablet, capsule, pill, granule or powder to form the desired preparation. The coating composition of the present invention coats the central core element utilizing conventional methods known in the art. For example, the coating composition of the present invention may coat the central core in a fluidized bed or pan. Other examples include spraying or painting the suspension of the composition of the present invention onto the formulation; and immersing the core element suspension of the coating composition of the present invention. Alternatively, the coating composition of the present invention is applied to the core element, e.g., the drug pellets, in a fluid bed bottom spray coater by having the pellets suspended in an air stream, and an aqueous dispersion of the coating composition is sprayed thereon. Various conventional coating apparatuses may be employed to facilitate this including, for example, a centrifugal fluidized bed coating apparatus, a pan coating apparatus, or a fluidized bed granulating coating apparatus. In the processes described herein, it is to be understood that during the coating of the core and/or after the core is completely coated, the solvent, i.e., water is removed by techniques known to one of ordinary skill in the art such as by drying or curing, and the like. As used herein, the term "coating" or "coat" or synonyms thereto includes both the process of applying the coating composition of the present invention to the core and the concomitant removal of the solvent, e.g., water, by techniques known to one of ordinary skill in the art, e.g., drying or curing thereof in which substantially all of the solvent e.g., water, in the coating composition is removed.

In one example, the coating layer is applied to the active core using a WURSTER bottom spray coater until the desired coating thickness is obtained. A Wurster fluidized-bed system is one in which an air jet, injected from underneath, fluidize the core material and effects drying while the coating is sprayed.

The coated active cores are then dried under conditions effective for drying e.g. in an oven or by means of gas in a fluidized bed under the conditions described above.

Alternatively, the coating can be applied to the active core using a conventional coating pan or an automated system, such as CF granulator, a fluidized bed process or any other suitably automated coating equipment.

The coating is applied so as to substantially uniformly and rapidly contact and coat the core. It is preferred that the coating composition has substantially an uniform thickness around the core.

Fluidized-bed processes are particularly suitable for coating small particles.

The amount of coating applied is sufficient to retard the release of the active component at a desired state. By varying the proportion of the coating on the core, different dissolutions of the active ingredient are obtained. The coating composition is applied to the core in a thickness sufficient to obtain the desired release profile of a therapeutically active agent when the coated substrate is exposed to aqueous solutions. Thus, by decreasing or increasing the thickness of the core, the dissolution profile is varied, but the composition of the core and the coating layer remain the same. Preferably, the coating composition is applied to the core at a thickness ranging from about 1% to about 15% by dry weight of the composition and more preferably from about 2% to about 10 and even more preferably from about 3 to about 6% of the composition. That is, when the coating composition according to the present invention is applied to the core, the pharmaceutical composition resulting therefrom is generally only 1 to about 15% heavier than the pharmaceutical composition containing just the core prior to the application of the coating, and more preferably from about 2 to about 10% heavier. Thus, the coating preferably constitutes from about 3 to about 6% by weight and most preferably from about 3.5 to about 5% by weight of the pharmaceutical composition. The core onto which the coating is applied contains the active component. The core may be a tablet, pellet; sphere or any other solid unit dosage form used normally in the pharmaceutical arts.

In another embodiment, the amount of coating on the core ranges from 0.5% to about 20% of the core. It is more preferred that the amount of coating on the core ranges from about 2% to about 10% by weight of the core. It is even more preferred that the amount of coating on the core ranges from about 3% to about 7% by weight of the core.

Without wishing to be bound, it is believed that the coating composition functions as follows. It is critical that the soluble component is completely soluble in the coating dispersion. Upon contact with the aqueous medium, the soluble component dissolves and makes the coat porous and progressively weaker. It diffuses out in the medium or environment of use. After substantially all of the soluble component is in solution state within the polymer or has been released in the external medium, there remains the porous insoluble polymer structure which controls the drug release. The aqueous medium of the gastrointestinal tract comes in contact with the inner core which causes the drug to dissolve and be released through the pores of the coating, allowing controlled release. Alternatively, if the core contains an agent of swelling, it may disrupt the coating which is then weakened and the drug is released as a burst. Such action would be a way to delay the release of the active component. The inner core as indicated hereinabove may contain swellable polymers capable of exerting controlled release of the drug.

It is very important to note that the films formed with the addition of the soluble component are weaker than the film formed by using the insoluble polymer latex alone. The film is formed by the coalescence of the polymer latex particles. The presence of the water soluble component which is not soluble or physically compatible with the polymer would prevent complete coalescence of the polymeric particles and thus produces a weaker film. At high concentrations the water soluble component will help cause erosion of the film.

Thus, it is critical that the water soluble component is soluble in water and the solubility is in excess of 5% (w/w). Once it is completely dissolved, it is homogenously dispersed in the coating. This component also helps improve the adhesion of the coat to the core. The low molecular weight and the water solubility helps diffuse the soluble component from the coat, leaving the coat microporous to allow drug release.

The present coating composition has several advantages over the other coating compositions in the prior art.

1. It is completely aqueous, so it is safer. As a completely aqueous medium there is an avoidance of organic solvents, which have inherent safety concerns, inflammability, carcinogenicity, environmental concerns costs, safety in general. It is also very simple to make.

2. The present coating composition has several advantages over hydrophilic polymers or water soluble polymers, such as polyvinylpyrollidone, polyhydroxypropylmethylcellulose or hydroxypropyl cellulose, that have been used to make the water insoluble coat wettable or hydratable. The use of such materials allows rapid diffusion of water through the coat. These materials also make the coat weaker because of inherent swelling properties. These materials have a very low diffusion coefficient, and they are not released in water to create porosities. If the core contains an agent capable of swelling rapidly, such coatings would rupture rapidly because of the movement of water through the coat as well as the imperfections of the coat.

On the other hand, in the present invention, without wishing to be bound, it is believed the low molecular weight component dissolves and exerts osmotic pressure within the coat, preventing rapid movement of water through the coat. The uniformly dispersed component allows uniform wetting of the coat, which is completely different from the coating containing heterodispersed particles therein. The uniform distribution of the coat allows better adhesion to the water wettable core. Most importantly, if the inner core contains hydrogels capable of swelling, the movement of water through the coat is uniform permitting uniform swelling of the matrix. The improved adhesive, the uniform wetting and movement of the medium also prevents premature rupture of the coat resulting from imperfections therein.

3. The coat is wettable.

4. The rate of release can be controlled by controlling the porosity of the coat which is in turn dependent upon the concentration of the soluble component. Alternatively, the rate of release can be controlled by the thickness of the coat.

5. Since the water soluble component is uniformly dispersed in the coat, it yields better uniformity of dry release between tablets.

Unless indicated to the contrary, weights are by dry weight.

The terms "cores" and "substrate", are used herein as synonyms and are used interchangeably as used herein, the singular can note the plural and vice versa.

By "sustained release" it is meant for purposes of the present invention that the therapeutically active medicament or drug is released from the formulation at a controlled rate such that therapeutically beneficial blood levels (but below toxic levels) of the medicament are maintained over an extended period of time, e.g., providing 4, 8, 12, 16, or 24 hours dosage form.

The present formulation comprises a pharmaceutical composition in unit dosage form. The term "unit dosage form", as employed herein, refers to a physically discrete unit suitable as unitary dosage to mammals, including humans, with each unit containing a predetermined quantity of active material calculated to produce the desired effect in association with the carrier, the lubricant and other ingredients of the formulation as described herein.

By "environment of use" is meant the aqueous environment into which the dosage form is placed. Commonly, this will be the gastrointestinal tract of a human or other animal.

The phrase "formulating the latex film coating", refers to the formation of aqueous dispersion of the polymer coating material prior to application to the oral unit dosage form. Any of the well known techniques involved in creating a polymeric film coating or latex may be employed.

The term "latex" refers to the aqueous colloidal dispersion of natural synthetic or semi-synthetic polymers, for example: natural lattices which occur as the natural products of certain plants and trees; synthetic lattices obtained by emulsion polymerization. Their adsorption at the interface lowers the interfacial tension between the dispersed and continuous phases and surrounds the particles with a firmly bound water envelope, stabilizing the emulsion against coagulation. The adsorbed layers of amphipathic surfactants are oriented in such a way that their hydrophilic polar heads are pointing into the continuous phase while the hydrophobic non-polar tails are anchored in the dispersed phase.

For industrial purposes, latexes are often produced by emulsion polymerization. A monomer or mixture of monomers is emulsified in water and polymerization is induced in the aqueous phase by an initiator. Surfactants play an important role in emulsion polymerization. Their adsorption at the interface lowers the interfacial tension between the dispersed and continuous phases and surrounds the particles with a firmly bound water envelope, stabilizing the emulsion against coagulation. The adsorbed layers of amphipathic surfactants are oriented in such a way that their hydrophilic polar heads are pointing into the continuous phase while the hydrophobic non-polar tails are anchored in the dispersed phase.

Other classes of polymers and resins such as the celluloses used in the instant invention which can not be produced as lattices by emulsion polymerization may be prepared in latex form by post emulsification of the presynthesized polymer. Surfactants also play an important role in stabilization of lattices made by these methods.

The controlled release formulation of the present invention is to be administered to mammals in need of such treatment wherein the medicament present in the formulation is administered in effective amounts.

The following non-limiting examples further illustrate the present invention.

EXAMPLE 1

A tablet was formed by thoroughly mixing 180 mg verapamil HCl, 15 mg Xanthan Gum, 300 mg of silicified microcrystalline cellulose 5 mg magnesium stearate in a blender at room temperature until homogenous. The above mixture was compressed using a tablet press.

A coating was prepared by mixing 480 g of an aqueous latex dispersion of ethyl cellulose (25% w/w dispersion), 30 g sucrose and 490 g of water until homogenous. The coating contained 15% w/w solids and a weight ratio of polymer-:sucrose of 4:1.

The tablets were coated by spraying using perforated side vented pans. A 2% coat (10 mg) was applied.

The Release profile thereof was determined with U.S.P. (U.S. Pharmacopoeia) apparatus I or II using water as the medium. The release profile is shown in FIG. 1. For comparative purposes, a release profile of the uncoated mixture was also obtained.

The results are shown in FIG. 1. As clearly shown by the graph, there was virtually no sustained release in the uncoated tablet, its contents were substantially released within an hour. On the other hand, the coated tablet exhibited a sustained release profile, 20% of the drug was released in about four hours, 40% of the drug was released in about six hours, and about 80% of the drug was released in about eight hours.

EXAMPLE 2

A 300 mg glipizide tablet was prepared by mixing 10 mg glipizide, 9 mg xanthan gum, 278 mg maltodextrin and 3 mg magnesium stearate in a blender at room temperature until homogenous. The resulting mixture was compressed into a tablet using a tablet press.

A coating was prepared by mixing 420 g of aqueous latex dispersion of ethyl cellulose (25% w/w dispersion), 45 g sucrose and 535 g water. The coating contained 15% w/w solids, and the weight ratio of polymer:sucrose was 70:30.

The tablets were coated by spraying using perforated side vented pans. A 3% coat (9 mg) was applied.

EXAMPLE 3

The procedure of Example 2 was repeated except that the coating dispersion contained a polymer:sucrose ratio of 90:10.

Figure 2:
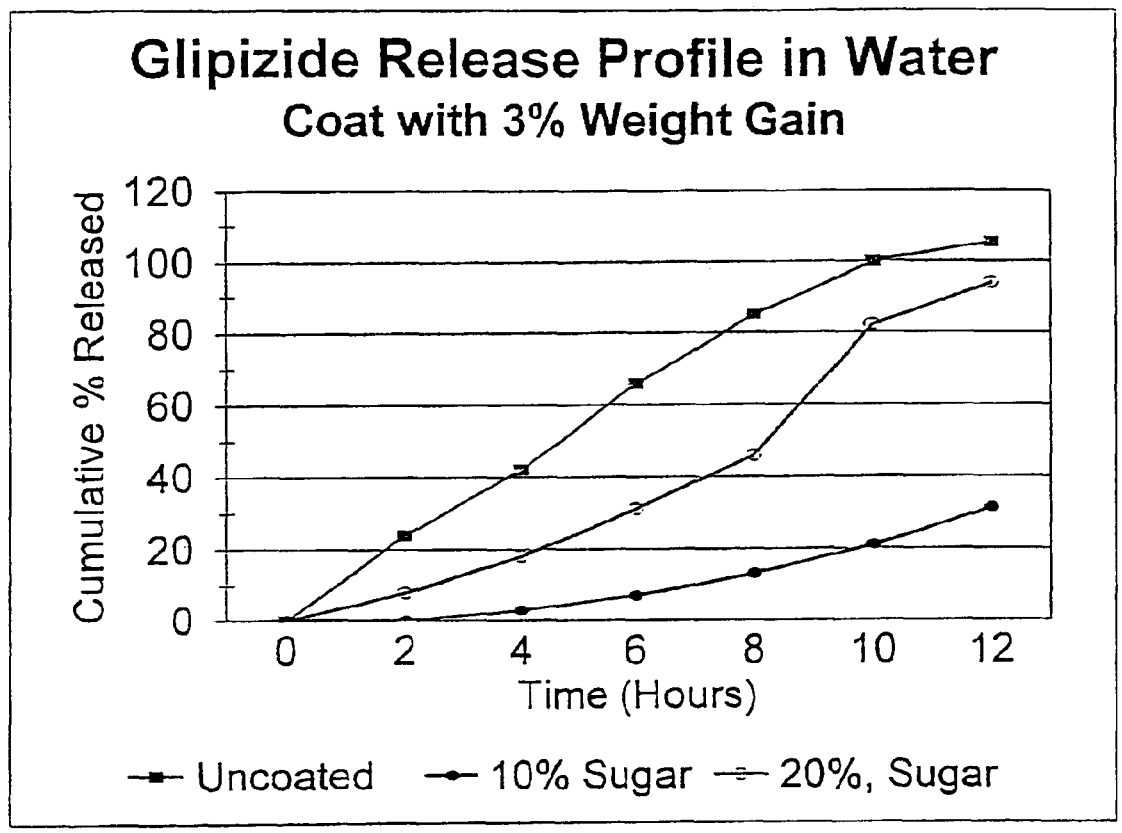
FIG. 2 graphically shows the difference in the dissolution rate of Glipizide tablet which is a highly water insoluble, without a coating and with two different coating compositions prepared in accordance with the present invention.

The release pattern of tablets of Example 2 and 3 as well as an uncoated tablet were determined with a U.S.P. apparatus I or II using water as the medium. The results are shown in FIG. 2. As clearly shown by the data, the use of the coating composition retards the release of the glipizide relative to the non-coated data. In addition, the data also shows that an increased concentration of sucrose resulted in a faster release rate of the active component relative to a composition containing less sugar; of course such a composition had a significantly slower release rate than that of the uncoated tablet.

EXAMPLE 4

A tablet was prepared by mixing 200 mg tramadol, 25 mg xanthan gum, 75 mg hydroxypropylmethyl cellulose (METHOCEL E-10M), 48.75 mg dicalcium phosphate dihydrate, 146.25 mg maltodextrin and 5 mg magnesium stearate until homogenous. The resulting mixture was compressed using a tablet press.

The coating was prepared as in Example 1 wherein the polymer:sucrose ratio was 4:1 and contained 15% w/w solids.

The tablets were coating by spraying using perforated side vented pans. A 3% w/w (15 mg) coating was applied.

EXAMPLE 5

The procedure of Example 4 was repeated except that the coating contained a weight ratio of polymer:sucrose of 90:10.

Figure 3:
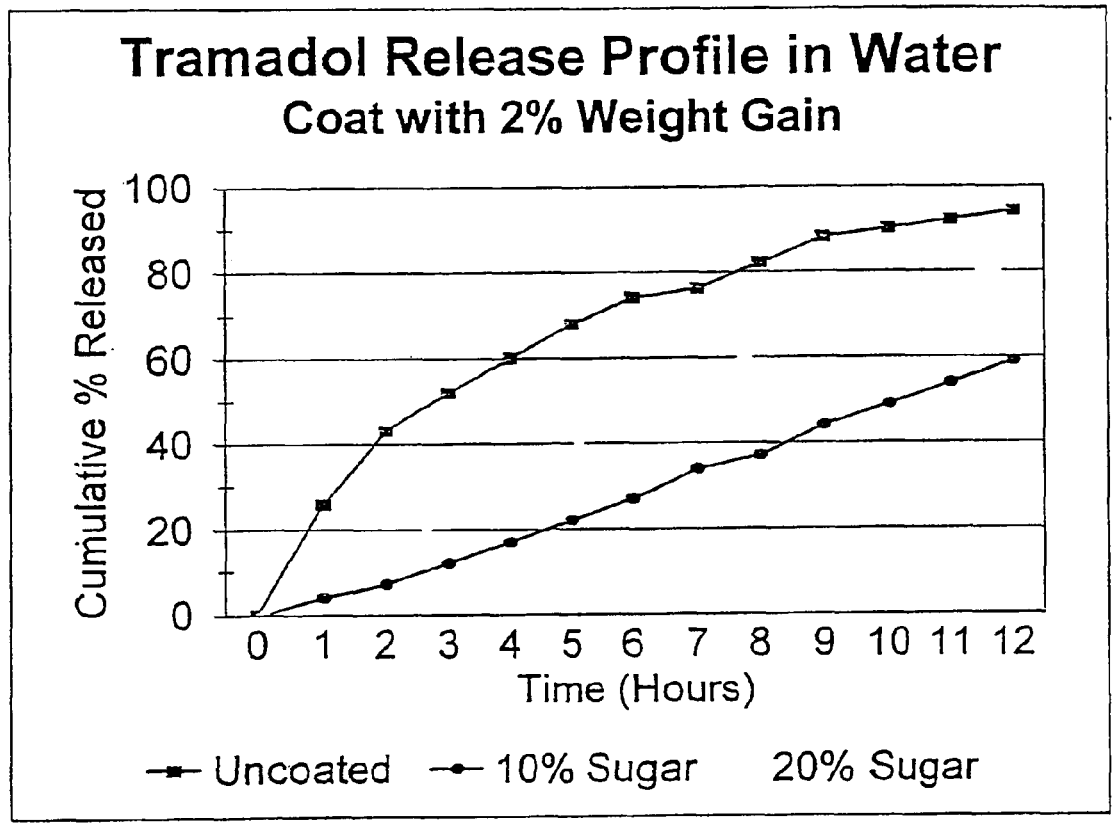
FIG. 3 graphically depicts shows the difference in the dissolution rate of a Tramadol coating without a coating and with two different coating compositions prepared in accordance with the present invention.

The release pattern of the tablets of Examples 4 and 5 as well as the uncoated tablet were determined with U.S.P. apparatus I and II using water as the medium. The results are depicted in FIG. 3.

As clearly shown by the data, the use of a coating composition of the present invention retards the release rate of the tramadol. In addition, as the data clearly show, when the coating composition contains a higher amount of sucrose, there was faster release of the tramadol relative to the tablet having a coating composition containing less sugar.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed:

1. A coating composition for coating a solid dosage form of a medicament, where the coating composition controls the release of the medicament, said coating composition comprising:
   (a) at least 50% (w/w) by dry weight of a water insoluble polymer insoluble in both acidic, basic and neutral pH, present in the form of an aqueous latex dispersion,
   (b) a water soluble component present in a weight ratio of about 5 to about 50% (w/w) by dry weight of the coating, said water soluble component being organic and either solid or liquid and said water soluble component being selected from the group consisting of polydextrose, polyalcohol or ester of polyalcohol, a non-polymeric sugar, a non-polymeric sugar alcohol and amino acid, said ratio of water insoluble polymer to water soluble component ranging from about 95:5 to about 1:1, the solid content in the coating composition ranging from about 5% to about 25%, said water soluble component being completely dissolved in the aqueous latex dispersion.

2. The coating composition according to claim 1 wherein the ratio of water insoluble polymer to water soluble component ranges from about 90:10 to about 1:1.

3. The coating composition according to claim 1 wherein the water soluble component has a molecular weight of less than 1000 daltons but greater than 100 daltons.

4. The coating composition according to claim 1 wherein the water soluble component is a sugar or sugar alcohol.

5. The coating composition according to claim 4 where the sugar is a monosaccharide, dissaccharide or trisaccharide.

6. The coating composition according to claim 5 wherein the sugar is sucrose.

7. The coating composition according to claim 1 wherein the water insoluble polymer is cellulose ether, cellulose ester, or copolymers of methylacrylate and acrylate, all in the form of a latex dispersion.

8. The coating composition according to claim 7 wherein the water insoluble polymer is ethylcellulose in the form of a latex dispersion.

9. The coating composition according to claim 1 wherein the weight ratio of water insoluble polymer to water soluble component ranges from about 90:10 to about 70:30.

10. The coating composition according to claim 9 wherein the weight ratio is 80:20.

11. The coating composition according to claim 1 wherein the water soluble component is polyalcohol.

12. The coating composition according to claim 1 wherein the water soluble component is an ester of a polyalcohol.

13. The coating composition according to claim 1 wherein the water soluble component is polydextrose.

14. A sustained release pharmaceutical composition in unit dosage form comprising a coating and a core, the core comprising a therapeutically effective amount of a medicament in association with a pharmaceutical carrier in solid unit dosage form, said core being uniformly coated with the coating composition comprising:
   (a) at least 50% (w/w) by dry weight of a water insoluble polymer insoluble in both acidic, basic and neutral pH, present in the form of an aqueous latex dispersion,
   (b) a water soluble component present in a weight ratio of about 5 to about 50% (w/w) by dry weight of the coating, having a molecular weight of less than about 15,000 daltons and water solubility in excess of 5 grams per 100 grams of water at room temperature and at 1 atm pressure, said water soluble component being organic and either solid or liquid, said water soluble component either being non-polymeric or polydextrose, polyalcohol or an ester of polyalcohol, said ratio of water insoluble polymer to water soluble component ranging from about 95:5 to about 1:1, the solid content in the coating composition ranging from about 5% to about 25%, said water soluble component being completely dissolved in the aqueous latex dispersion, wherein the medicament is a drug selected from the group consisting of tramadol, glipizide, metoprolol, pseudoephedrine, oxybutynin, nifedipine, metformin, diltiazem, enalapril, verapamil and mesalamine or a pharmaceutically acceptable salt of said drug.

15. A sustained release pharmaceutical composition in unit dosage form comprising a coating and a core, the core comprising a therapeutically effective amount of a medicament in association with a pharmaceutical carrier in solid unit dosage form, said core being uniformly coated with the coating composition according to claim 1.

16. The pharmaceutical composition according to claim 15 wherein the solid dosage form is in the form of a tablet or pill.

17. The pharmaceutical composition according to claim 15 wherein the solid dosage form is in the form of a pellet or bead.

18. The pharmaceutical composition according to claim 15 wherein the core contains xanthan gum.

19. The pharmaceutical composition according to claim 15 wherein the core contains a water soluble cellulose ether.

20. The pharmaceutical composition according to claim 15 wherein the core contains a xanthan gum and cellulose ether.

21. The pharmaceutical composition according to claim 15 wherein the core contains buffer salts capable of exerting osmotic pressure.

22. The pharmaceutical composition according to claim 15 wherein the core contains a controlled release tablet.

23. The pharmaceutical composition according to claim 15 wherein the medicament is a drug selected from the group consisting of tramadol, glipizide, metoprolol, pseudoephedrine, oxybutynin, nifedipine, metformin, diltiazem, enalapril, verapamil or mesalamine or a pharmaceutically acceptable salts of said drug.

24. The pharmaceutical composition according to claim 15 wherein the amount of coating on the core ranges from 0.5 to about 20% by weight of the core.

25. The pharmaceutical composition according to claim 24, wherein the amount of coating on the core ranges from about 2% to about 10% by weight of the core.

26. The pharmaceutical composition according to claim 24, wherein the amount of coating on the core ranges from about 3% to about 7% by weight of the core.

27. A method of treating a patient with an orally administrable time-release drug comprising administering to said patient in need of treatment a therapeutically effective amount of the pharmaceutical composition according to claim 15.

28. A method of preparing a sustained release pharmaceutical composition which comprises coating a core thereof, said pharmaceutical composition comprising a therapeutically effective amount of a medicament in association with a pharmaceutical carrier in solid unit dosage form, and said coating composition comprising:
   (a) at least 50% (w/w) by dry weight of a water insoluble polymer insoluble in both acidic, basic and neutral pH, present in the form of an aqueous latex dispersion,
   (b) a water soluble component present in a weight ratio of about 5 to about 50% (w/w) by dry weight of the coating, said water soluble component being organic and either solid or liquid and said water soluble component being selected from the group consisting of polydextrose, a polyalcohol or ester of polyalcohol, a non-polymeric sugar, a non-polymeric sugar alcohol, and amino acid, said ratio of water insoluble polymer to water soluble component ranging from about 95:5 to about 1:1, the solid content in the coating composition ranging from about 5% to about 25%, said water soluble component being completely dissolved in the aqueous latex dispersion.

29. A coating composition for coating a solid dosage form of a medicament, where the coating composition controls the release of the medicament, said coating composition comprising:
   (a) at least 50% (w/w) by dry weight of a watch insoluble polymer insoluble in both acidic, basic and neutral pH, present in the form of an aqueous latex dispersion, (b) a second component consisting of a water soluble component which is non-ionic and is not a polymer or which is polyalcohol or ester of polyalcohol or polydextrose, said water soluble component being present in a weight ratio of about 5 to about 50% (w/w) by dry weight of the coating, having a molecular weight of less than about 15,000 daltons and water solubility in excess of 5 grams per 100 grams of water at room temperature and at 1 atm pressure, said water soluble component being organic and either solid or liquid; said ratio of water insoluble polymer to water soluble component ranging from about 95:5 to about 1:1, and (c) a plasticizer, the solid content in the coating composition ranging from about 5% to about 25%, said water soluble component being completely dissolved in the aqueous latex dispersion.

30. The coating composition according to claim 29 wherein the ratio of water insoluble polymer to water soluble component ranges from about 90:10 to about 1:1.

31. The coating composition according to claim 29 wherein the water soluble component has a molecular weight of less than 1000 daltons but greater than 100 daltons.

32. The coating composition according to claim 29 wherein the water soluble component is a sugar or sugar alcohol.

33. The coating composition according to claim 32 where the sugar is a mono saccharide, dissaccharide or trisaccharide.

34. The coating composition according to claim 33 wherein the sugar is sucrose.

35. The coating composition according to claim 29 wherein the water insoluble polymer is cellulose ether, cellulose ester, or copolymers of methylacrylate and acrylate, all in the form of a latex dispersion.

36. The coating composition according to claim 29 wherein the water insoluble polymer is ethylcellulose in the form of a latex dispersion.

37. The coating composition according to claim 29 wherein the weight ratio of water insoluble polymer to water soluble component ranges from about 90:10 to about 70:30.

38. The coating composition according to claim 37 wherein the weight ratio is about 80:20.

39. The coating composition according to claim 29 wherein the water soluble component is polyalcohol.

40. The coating composition according to claim 29 wherein the water soluble component is an ester of a polyalcohol.

41. The coating composition according to claim 29 wherein the water soluble component is polydextrose.

42. The coating composition according to claim 29 wherein the plasticizer is glycerin, propylenglycol, or polyethyleneglycol.

43. A sustained release pharmaceutical composition in unit dosage form comprising a coating and a core, the core comprising a therapeutically effective amount of a medicament in association with a pharmaceutical carrier in solid unit dosage form, said core being uniformly coated with the coating composition according to claim 29.

44. The pharmaceutical composition according to claim 43 wherein the solid dosage form is in the form of a tablet or pill.

45. The pharmaceutical composition according to claim 43 wherein the solid dosage form is in the form of a pellet or bead.

46. The pharmaceutical composition according to claim 43 wherein the core contains xanthan gum.

47. The pharmaceutical composition according to claim 43 wherein the core contains a water soluble cellulose ether.

48. The pharmaceutical composition according to claim 43 wherein the core contains xanthan gum and a water soluble cellulose ether.

49. The pharmaceutical composition according to claim 43 wherein the core contains buffer salts capable of exerting osmotic pressure.

50. The pharmaceutical composition according to claim 43 which is a controlled release tablet.

51. The pharmaceutical composition according to claim 43 wherein the medicament is a drug selected from the group consisting of tramadol, glipizide, metoprolol, pseudoephedrine, oxybutynin, nifedipine, metformin, diltiazem, enalapril, verapamil and mesalamine or a pharmaceutically acceptable salt of said drug.

52. The pharmaceutical composition according to claim 43 wherein the amount of coating of the core ranges from 0.5 to about 20% by weight of the core.

53. The pharmaceutical composition according to claim 52, wherein the amount of coating on the core ranges from about 2% to about 10% by weight of the core.

54. The pharmaceutical composition according to claim 53, wherein the amount of coating on the core ranges from about 3% to about 7% by weight of the core.

55. A method of treating a patient with an orally administrable time-release drug comprising administering to said patient in need of treatment a therapeutically effective amount of the pharmaceutical composition according to claim 43.

56. A method of preparing a sustained release pharmaceutical composition which comprises coating a core thereof, wherein said pharmaceutical composition comprises a therapeutically effective amount of a medicament in associating with a pharmaceutical carrier in solid unit dosage form, and said coating composition comprising:

(a) at least 50% (w/w) by dry weight of a water insoluble polymer insoluble in both acidic, basic and neutral pH, present in the form of an aqueous latex dispersion, (b) a second component which is a water soluble component which is non-ionic and is not a polymer or which is a polyalcohol or ester thereof or polydextrose, said water soluble component being present in a weight ratio of about 5 to about 50% (w/w) by dry weight of the coating, having a molecular weight of less than about 15,000 daltons and water solubility in excess of 5 grams per 100 grams of water at room temperature at 1 atm pressure, said water soluble component being organic and either solid or liquid, said ratio of water insoluble polymer to water soluble component ranging from about 95:5 to about 1:1, and (c) a plasticizer, wherein the solid content in the coating composition ranges from about 5% to about 25%, said water soluble component being completely dissolved in the aqueous latex dispersion.

57. A sustained release pharmaceutical composition in unit dosage form comprising a coating and a core, the core comprising a therapeutically effective amount of a medicament in association with a pharmaceutical carrier in solid unit dosage form, said core being uniformly coated with a coating composition comprising:

(a) at least 50% (w/w) by dry weight of a water insoluble polymer insoluble in both acidic, basic and neutral pH, present in the form of an aqueous latex dispersion, (b) a water soluble component present in a weight ratio of about 5 to about 50% (w/w) by dry weight of the coating, having a molecular weight of less than about 15,000 daltons and water solubility in excess of 5 grams per 100 grams of water at room temperature and at 1 atm pressure, said water soluble component being organic and either solid or liquid, said water soluble component is either non-polymeric or is polydextrose, polyalcohol or ester of polyalcohol, said ratio of water insoluble polymer to water soluble component ranging from about 95:5 to about 1:1, the solid content in the coating composition ranges from about 5% to about 25%, said water soluble component being completely dissolved in the aqueous latex dispersion, wherein the core contains xanthan gum, a water soluble cellulose ether, a mixture of xanthan gum and a water soluble cellulose ether or buffer salts capable of exerting osmotic pressure.

58. The pharmaceutical composition according to claim 57 wherein the solid dosage form is in the form of a tablet or pill.

59. The pharmaceutical composition according to claim 57 wherein the solid dosage form is in the form of a pellet or bead.

60. The pharmaceutical composition according to claim 57 wherein the core contains xanthan gum.

61. The pharmaceutical composition according to claim 57 wherein the core contains a water soluble cellulose ether.

62. The pharmaceutical composition according to claim 57 wherein the core contains xanthan gum and a water soluble cellulose ether.

63. The pharmaceutical composition according to claim 57 wherein the core contains buffer salts capable of exerting osmotic pressure.

64. The pharmaceutical composition according to claim 57 which is a controlled release tablet.

65. The pharmaceutical composition according to claim 57 wherein the medicament is a drug selected from the group consisting of tramadol, glipizide, metoprolol, pseudoephedrine, oxybutynin, nifedipine, metformin, diltiazem, enalapril, verapamil and mesalamine or a pharmaceutically acceptable salt of said drug.

66. The pharmaceutical composition according to claim 57 wherein the amount of coating on the core ranges from 0.5 to about 20% by weight of the core.

67. The pharmaceutical composition according to claim 66, wherein the amount of coating on the core ranges from about 2% to about 10% by weight of the core.

68. The pharmaceutical composition according to claim 67, wherein the amount of coating on the core ranges from about 3% to about 7% by weight of the core.

69. A method of treating a patient with an orally administering time-release drug comprising administering to said patient in need of treatment a therapeutically effective amount of the pharmaceutical composition according to claim 57.

70. A sustained release pharmaceutical composition in unit dosage form comprising a coating and a core, the core comprising a therapeutically effective amount of a medicament in association with a pharmaceutical carrier in solid unit dosage form, said core being uniformly coated with a coating composition comprising:

(a) at least 50% (w/w) by dry weight of a water insoluble polymer insoluble in both acidic, basic and neutral pH, present in the form of an aqueous latex dispersion, (b) a water soluble component present in a weight ratio of about 5 to about 50% (w/w) by dry weight of the coating, having a molecular weight of less than about 15,000 daltons and water solubility in excess of 5 grams per 100 grams of water at room temperature and at 1 atm pressure, said water soluble component being organic and either solid or liquid, said water soluble component being non-polymeric or polydextrose or polyalcohol or ester of polyalcohol, said ratio of water insoluble polymer to water soluble component ranging from about 95:5 to about 1:1, the solid content in the coating composition ranging from about 5% to about 25%, said water soluble component being completely dissolved in the aqueous latex dispersion, wherein the amount of coating on the core ranges from about 0.5 to about 20% by weight of the core.

71. The pharmaceutical composition according to claim 70 wherein the medicament is a drug selected from the group consisting of tramadol, glipizide, metoprolol, pseudoephedrine, oxybutynin, nifedipine, metformin, diltiazem, enalapril, verapamil and mesalamine or a pharmaceutically acceptable salt of said drug.

72. The pharmaceutical composition according to claim 70 wherein the amount of coating on the core ranges from about 2% to about 10% by weight of the core.

73. The pharmaceutical composition according to claim 70 wherein the amount of coating on the core ranges from about 3% to about 7% by weight of the core.

74. A method of treating a patient with an orally administrable time-release drug comprising administering to said patient in need of treatment a therapeutically effective amount of the pharmaceutical composition according to claim 70.

75. A method of treating a patient with an orally administrable time-release drug comprising administering to said patient in need of treatment a therapeutically effective amount of a sustained release pharmaceutical composition in unit dosage form comprising a coating and a core, the core composing a therapeutically effective amount of a medicament in association with a pharmaceutical carrier in solid unit dosage form, said core being uniformly coated with a coating comprising:

(a) at least 50% (w/w) by dry weight of a water insoluble polymer insoluble in both acidic, basic and neutral pH, present in the form of an aqueous latex dispersion, (b) a water soluble component present in a weight ratio of about 5 to about 50% (w/w) by dry weight of the coating, having a molecular weight of less than about 15,000 daltons and water solubility in excess of 5 grams per 100 grams of water at room temperature at 1 atm pressure, said water soluble component being organic and either solid or liquid, said water soluble component being non-polymeric or polydextrose, polyalcohol or ester of polyalcohol, said ratio of water insoluble polymer to water soluble component ranges from about 95:5 to about 1:1, the solid content in the coating composition ranges from about 5% to about 25%, said water soluble component being completely dissolved in the aqueous latex dispersion.

* * * * *